Sept. 23, 1958 F. W. ANDERSON Plant Pat. 1,756

PLUM TREE

Filed Feb. 4, 1958

WITNESS

Addison E. Avery

INVENTOR:

Frederic W. Anderson

Webster & Webster

ATTYS.

United States Patent Office

Plant Pat. 1,756
Patented Sept. 23, 1958

1,756

PLUM TREE

Frederic W. Anderson, Merced, Calif., assignor to Kim Bros., a copartnership doing business under the fictitious name and style of Reedley Nursery, Reedley, Calif.

Application February 4, 1958, Serial No. 713,275

1 Claim. (Cl. 47—62)

This invention relates to a new and distinct variety of plum tree having many of the desirable characteristics of the Santa Rosa and Eldorado plum varieties (both unpatented).

The Santa Rosa, ripening in the central valley of California during the last half of June, has long been the leading shipping plum in such state. The Eldorado, ripening later than the Santa Rosa, has—during the past few years—usually averaged a higher price on the auction markets than any other plum of its season.

I originated the herein claimed variety of plum tree in my experimental orchard, located near Merced, California, in the following manner:

Seeking to combine the best commercial characteristics of the above mentioned two popular varieties, I gathered a quantity of seeds from a row of Eldorado plum trees adjoining a block of Santa Rosa plum trees. As the Eldorado is a self-incompatible variety and does not set fruit with its own pollen, it was assumed that most of the resultant seedlings would be natural crosses between said two mentioned varieties.

More than eight hundred seedlings were grown from such seeds, and the variation was great in all characteristics; nearly all of such seedlings having been discarded as being inferior to present varieties for reasons such as lack of vigor of the trees, and inferior size, firmness, color, and eating quality of the fruit, together with growth cracks and numerous other defects.

However, a few of such seedlings which evidenced desirable tree and fruit characteristics were retained for further tests and were therefore top-worked on mature plum and nectarine trees in my experimental orchard, located as aforesaid. The instant variety was one of such top-workings, and upon careful observation by me was found to combine most of the best characteristics of each of the presumed parents, and I then selected the variety for further reproduction.

Subsequent to its origination and selection by me, such further reproduction of the variety was successfully asexually accomplished, likewise by top-working in my experimental orchard, and all of such top workings ran true to the parent in every respect.

The fruit of the present variety of plum tree has the attractive purple red color and good eating quality of the Santa Rosa; the firmness and remarkable shipping and keeping qualities of the Eldorado; and ripens about two weeks after the Eldorado and about a week after the Late Rosa (unpatented). Also, the fruit is of an average larger size than any of the above mentioned varieties when grown on comparable trees and under like soil and climatic conditions.

As compared with the Late Rosa the fruit of the present variety is of average larger size, firmer, keeps in good eating condition for a longer time, has a lighter and brighter exterior color, and at harvest has less culls due to growth cracks and other defects.

Figure 1:
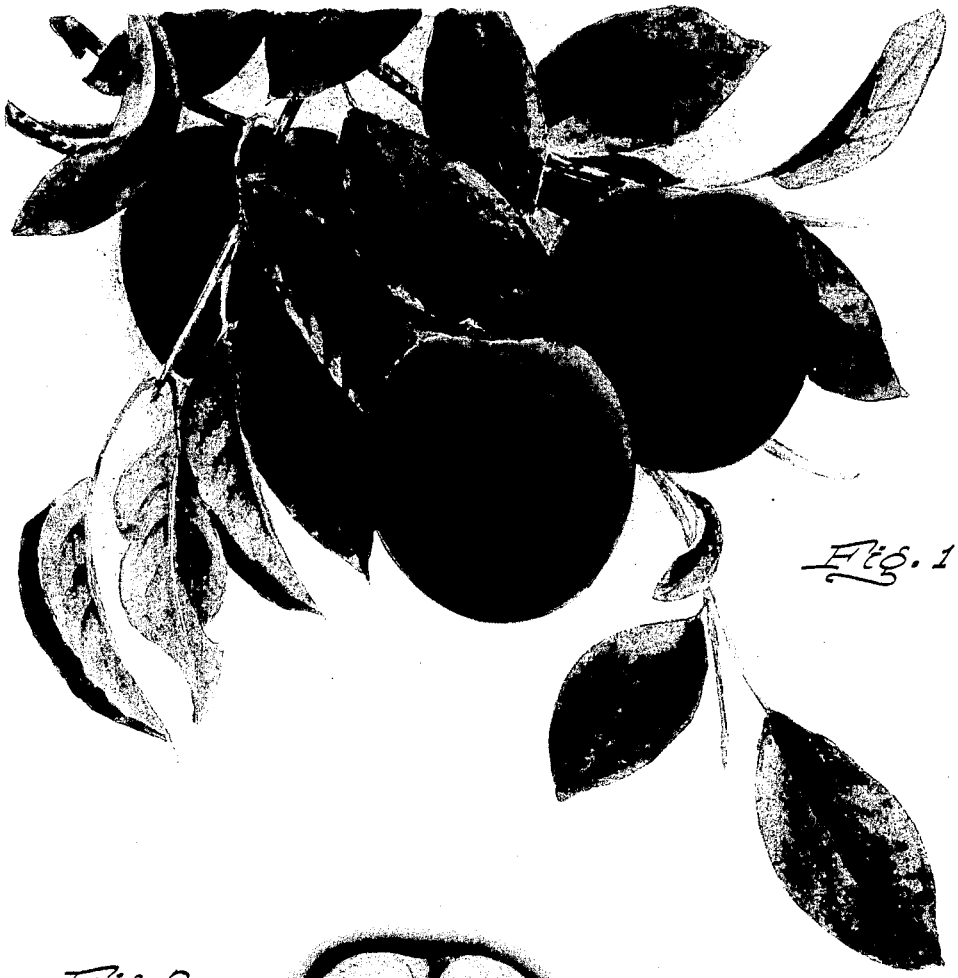
Fig. 1 is an elevation showing several of the plums, together with twigs and leaves.
Figure 2:
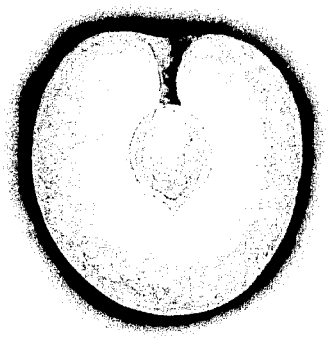
Fig. 2 is a sectional elevation of one of the plums, with the stone remaining in place.

Referring now more specifically to the homological details of this new and distinct variety of plum tree, the following is an outline description thereof; all major color plate identifications being by reference to Maerz and Paul Dictionary of Color, except where common terms of color definition are employed:

Tree:
- *Size.*—Large
- *Vigor.*—Vigorous.
- *Form.*—Spreading.
- *Density.*—Open.
- *Production.*—Productive.
- *Bearing.*—Regular bearer.

Trunk:
- *Size.*—Stocky.

Branches:
- *Size.*—Medium.

Leaves:
- *Size.*—Medium. Average length — 3". Average width—1⅛".
- *Form.*—Oval.
- *Thickness.*—Medium.
- *Margin.*—Crenate.
- *Petiole.*—Medium length.
- *Glands.*—Average number and position—usually two to three on blade and none on petiole. Small.
- *Color.*—Top side—Medium dark green (23–L–6). Under side—lighter green (22–G–6).

Flower Buds:
- *Size.*—Medium.
- *Length.*—Medium.

Flowers:
- *Blooming period.*—Approximately with the Santa Rosa plum; medium as compared with other varieties.

Fruit:
- *Maturity when described.*—Eating ripe.
- *Date of first picking.*—August 15, 1957.
- *Date of last picking.*—September 1, 1957.
- *Size.*—Large; uniform. Average diameter axially—2 to 2⅜". Average transversely in suture plane—2 to 2⅜".
- *Form.*—Uniform; symmetrical; globose.
- *Suture.*—Distinct; shallow.
- *Ventral Surface.*—Rounded; strongly lipped; lips equal.
- *Cavity.*—Rounded. Average depth—⅝". Average breadth—9/16".
- *Base.*—Rounded.
- *Apex.*—Short; depressed.

Skin:
- *Thickness.*—Medium.
- *Texture.*—Medium.
- *Tendency to crack.*—Slight.
- *Down.*—Wanting.
- *Color.*—Red (6–L–6 to 7–L–8), shading darker to a burgundy red (56–L–11); the general appearance of the fruit being a plum or purple red (47–J–9), with a light purple bloom.

Flesh:
- *Juice.*—Abundant to moderate; rich.
- *Texture.*—Firm; crisp; meaty.
- *Ripens.*—Even.
- *Flavor.*—Vinous.
- *Eating quality.*—Good to best.

*Color.*—Yellow (11–B–8 to 4–G–11), shading to red (5–L–6) near skin, with small yellowish streaks (9–D–5) near stone.

*Surface of pit cavity.*—Flesh yellow, with some red in the immediate flesh.

Stone:

*Type.*—Free to semi-free. Adheres to flesh along both dorsal and ventral edges.

*Size.*—Small. Average length—$^{13}/_{16}$". Average breadth—$^{9}/_{16}$". Average thickness—$^{5}/_{16}$".

*Form.*—Oval.

*Base.*—Straight.

*Apex.*—Rounded.

*Sides.*—Equal.

*Ventral edge.*—Thin.

*Dorsal edge.*—Full.

*Tendency to split.*—None.

*Color.*—Beige (11–A–7 to 11–R–8).

Use: Market; local; dessert; shipping.

Keeping quality: Good.

Shipping quality: Good.

The tree and its fruit herein described may vary in slight detail due to climatic and soil conditions under which the variety may be grown.

The following is claimed:

A new and distinct variety of plum tree, as illustrated and described, which bears large, uniform, globose, fruit having a purple red exterior color, yellow flesh which shades to red near the skin, and a free to semi-free stone; said fruit being characterized—in likeness to the Santa Rosa plum—by the purple red exterior color and good eating quality, and—in likeness to the Eldorado plum—by the firmness, of flesh and good shipping and keeping qualities thereof; and distinctively characterized by a ripening period about two weeks after the Eldorado plum and about a week after the Late Rosa plum; additionally characterized by larger size than said Santa Rosa, Eldorado and Late Rosa plums; and further characterized—as to the latter—by being firmer of flesh, remaining in good eating condition for a longer time, having a lighter and brighter exterior color, and less culls at harvest.

No references cited.